(12) United States Patent
Felix

(10) Patent No.: US 7,794,500 B2
(45) Date of Patent: Sep. 14, 2010

(54) SURGICAL IMPLANT

(76) Inventor: Brent A. Felix, 2911 E. Little Cottonwood Rd., Sandy, UT (US) 84092

( * ) Notice: Subject to any disclaimer, the term of this patent is extended or adjusted under 35 U.S.C. 154(b) by 160 days.

(21) Appl. No.: 11/147,487

(22) Filed: Jun. 8, 2005

(65) Prior Publication Data

US 2006/0089716 A1    Apr. 27, 2006

Related U.S. Application Data

(63) Continuation-in-part of application No. 29/230,492, filed on May 23, 2005, now Pat. No. Des. 524,942.

(60) Provisional application No. 60/623,009, filed on Oct. 27, 2004.

(51) Int. Cl.
*A61F 2/44* (2006.01)

(52) U.S. Cl. .................... 623/17.11; 606/246

(58) Field of Classification Search ... 623/17.11–17.16, 623/16.11
See application file for complete search history.

(56) References Cited

U.S. PATENT DOCUMENTS

| | | | |
|---|---|---|---|
| 4,834,757 A * | 5/1989 | Brantigan | 623/17.11 |
| 5,554,191 A | 9/1996 | Lahille et al. | |
| D374,286 S | 10/1996 | Goble et al. | |
| D374,482 S | 10/1996 | Goble et al. | |
| 5,609,636 A * | 3/1997 | Kohrs et al. | 623/17.16 |
| 5,658,337 A * | 8/1997 | Kohrs et al. | 623/17.11 |
| 5,766,252 A * | 6/1998 | Henry et al. | 623/17.16 |
| D397,439 S | 8/1998 | Koros et al. | |
| D403,069 S | 12/1998 | Drewry et al. | |
| 6,090,143 A | 7/2000 | Meriwether et al. | |
| 6,159,245 A | 12/2000 | Meriwether et al. | |
| 6,231,609 B1 | 5/2001 | Mehdizadeh | |
| 6,302,914 B1 | 10/2001 | Michelson | |
| 6,371,989 B1 | 4/2002 | Chauvin et al. | |
| 6,409,766 B1 | 6/2002 | Brett | |
| 6,432,107 B1 | 8/2002 | Ferree | |
| D462,766 S | 9/2002 | Jacobs et al. | |
| 6,454,807 B1 | 9/2002 | Jackson | |
| 6,488,710 B2 | 12/2002 | Besselink | |
| 6,520,993 B2 | 2/2003 | James et al. | |
| 6,537,320 B1 | 3/2003 | Michelson | |
| D473,944 S | 4/2003 | Anderson | |
| 6,613,091 B1 | 9/2003 | Zdeblick et al. | |
| 6,648,917 B2 | 11/2003 | Gerbec et al. | |
| 6,666,889 B1 | 12/2003 | Commarmond | |
| 6,669,700 B1 | 12/2003 | Farris et al. | |
| 6,676,703 B2 | 1/2004 | Biscup | |
| 6,695,882 B2 | 2/2004 | Bianchi et al. | |
| 6,712,852 B1 | 3/2004 | Chung et al. | |
| 6,743,255 B2 * | 6/2004 | Ferree | 623/17.11 |
| D493,533 S | 7/2004 | Blain | |

(Continued)

*Primary Examiner*—Eduardo C Robert
*Assistant Examiner*—Tara R Carter
(74) *Attorney, Agent, or Firm*—Workman Nydegger

(57) ABSTRACT

A surgical implant includes a first end plate having a substantially X-shaped configuration. A second end plate is spaced apart for the first end plate. A central longitudinal axis centrally extends between the first end plate and the second end plate. Four spaced apart beams extend from the first end plate to the second end plate at location spaced apart form the central longitudinal axis. An open passageway extends between each adjacent pair of the beams and intersects with the central longitudinal axis.

39 Claims, 9 Drawing Sheets

U.S. PATENT DOCUMENTS

| | | |
|---|---|---|
| 6,811,555 B1 | 11/2004 | Willis et al. |
| 6,824,565 B2 | 11/2004 | Muhanna et al. |
| 6,827,740 B1 | 12/2004 | Michelson |
| 6,852,126 B2 * | 2/2005 | Ahlgren .................. 623/17.11 |
| 6,855,166 B2 * | 2/2005 | Kohrs ..................... 623/17.11 |
| 6,913,621 B2 | 7/2005 | Boyd et al. |
| 7,192,447 B2 | 3/2007 | Rhoda |
| 2001/0039453 A1 | 11/2001 | Gresser et al. |
| 2002/0128652 A1 | 9/2002 | Ferree |
| 2002/0143401 A1 | 10/2002 | Michelson |
| 2002/0165613 A1 | 11/2002 | Lin et al. |
| 2003/0114931 A1 * | 6/2003 | Lee et al. ................ 623/17.11 |
| 2003/0139812 A1 * | 7/2003 | Garcia et al. ............ 623/17.11 |
| 2004/0034430 A1 | 2/2004 | Falahee |
| 2004/0199251 A1 | 10/2004 | McCombe et al. |
| 2005/0021144 A1 * | 1/2005 | Malberg et al. .......... 623/17.11 |
| 2005/0216081 A1 | 9/2005 | Taylor |

* cited by examiner

SURGICAL IMPLANT

CROSS-REFERENCE TO RELATED APPLICATIONS

This application is a continuation-in-part of U.S. patent application Ser. No. 29/230,492, filed May 23, 2005 U.S. Pat. No. Des. 524,942 and claims priority to U.S. Provisional Patent Application Ser. No. 60/623,009, filed Oct. 27, 2004, which applications are incorporated herein by specific reference.

BACKGROUND OF THE INVENTION

1. The Field of the Invention

The present invention relates generally to surgical devices and methods for supporting bone or other tissues and, more specifically, to surgical devices and methods for fusing adjacent vertebrae or other bones.

2. The Relevant Technology

The spinal column is made up of thirty-three vertebrae, each separated by an intervertebral disc. Each disc is slightly compressible, thereby allowing the vertebra above a disc to move relative to the vertebra below the disc. This unique design allows the spine to bend in many directions. The intervertebral discs absorb pounding and compressive forces throughout the lifetime of a person. Through disease, trauma, or normal wear, an intervertebral disc can become damaged or ruptured, thereby creating instability that leads to loss of function and excruciating pain. Such persons often turn to surgery to remove the damaged disc and fuse the corresponding adjacent vertebrae together.

During surgery, the damaged disc is removed and a spinal fusion implant is inserted to replace the damaged disc and restore the spacing between the vertebrae. The spinal implant typically has a thickness corresponding to the thickness of the disc being removed and has openings extending therethrough. To facilitate permanent fusion between vertebrae, the openings of the implant are typically packed with an osteogenic substance. The osteogenic substance promotes the rapid growth of a bony column between the vertebrae. Once the vertebrae are fused, the two adjacent vertebrae act as one, rigid vertebrae.

When first inserted, the osteogenic substance is not sufficiently strong to withstand the compressive forces applied by the vertebrae. Hence the need for the implant. The osteogenic substance promotes the bone growth between the vertebrae until the bone growth fuses the vertebrae together and can independently withstand the compressive forces applied by the vertebrae. This fusion process can take several months to complete.

Although the osteogenic substance is not initially strong enough to withstand the full compressive force that a healthy disc can handle, bone growth produced by the osteogenic substance is greatly benefited by the osteogenic substance being subject to a compression force when first implanted. That is, for the osteogenic substances to form the bony growth between the vertebrae, the osteogenic substance should be firmly compressed between the vertebrae to prevent the osteogenic substance from moving or sheering relative to the bone. If the osteogenic substance is not compressed firmly between the bone, sheering or movement can occur leading to only a partial fusing or even no fusing to occur. Under such situations, surgery is often required to remove the implant and repeat the procedure.

Although there are many different implants that have been used to fuse vertebrae together, conventional implants can suffer from a number of shortcomings. For example, to withstand the compressive force initially produced by the vertebrae, many conventional implants have been structurally reinforced to such an extent that they have substantially no or minimal compression during use. As a result of the rigid structure of the implant, the osteogenic substance housed within the implant is not properly compressed between the vertebrae to effectively produce the bone growth as discussed above. The lack of compression of the osteogenic substance as a result of the implant is referred to as stress shielding.

Furthermore, the structural reinforcing of many conventional implants has been designed such that it limits the number of openings formed on and extending through the implant. As a result, it can be difficult for the bone growth to extend through the implant so as to fuse the adjacent bone together.

Other implants permit flexing at portions of the implant but fail to permit flexing along the full length of the implant, thereby minimizing the effective use of the osteogenic substance. Still other implants accommodate compression or minimize the need for compression by being formed from multiple parts that enable expansion of the implant between the vertebrae. Expandable implants, however, are typically more expensive, requiring special insertion and expansion tools, and can increase the complexity and time for implanting. Expandable implants can also have a high risk of failure under compression.

Accordingly, what is needed in the art are improved bone fusion implants that are simple and easy to implant, that provide desirable compression along the full length thereof so as to optimize bone growth produced by an osteogenic substance, and that are sufficiently open to enhance bone growth through and around the implant.

BRIEF DESCRIPTION OF THE DRAWINGS

Various embodiments of the present invention will now be discussed with reference to the appended drawings. It is appreciated that these drawings depict only typical embodiments of the invention and are therefore not to be considered limiting of its scope.

DETAILED DESCRIPTION OF THE PREFERRED EMBODIMENTS

Figure 1:
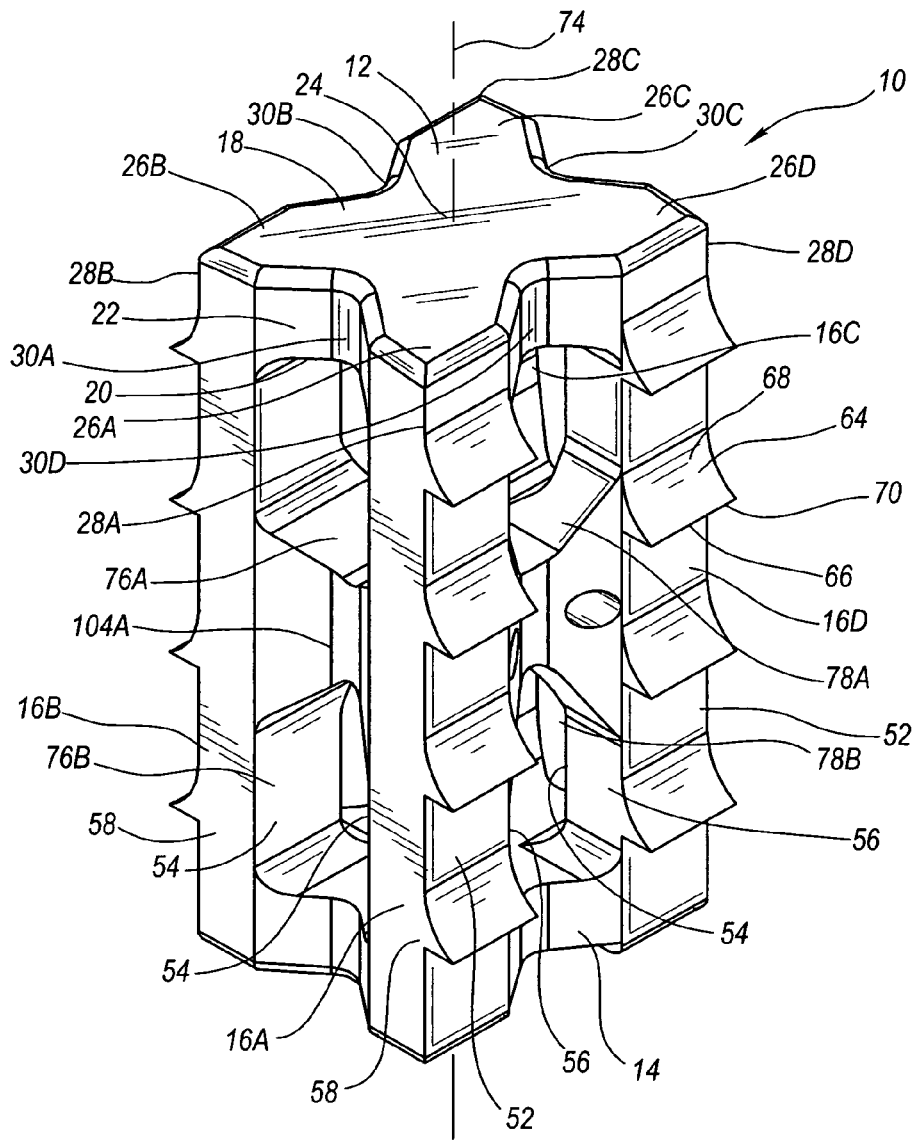
FIG. 1 is a perspective view of a surgical implant according to one embodiment of the present invention.

Depicted in FIG. 1 is one embodiment of an inventive surgical implant 10 incorporating features of the present invention. Surgical implant 10 is designed for placement between bones and/or pieces of bone to facilitate fusing of the bone matter together. For example, surgical implant 10 can be placed between adjacent vertebrae in the spine to facilitate fusing of the vertebrae together. Surgical implant 10 can also be used for purposes other than fusing bone together. For example, surgical implant 10 can also be used as a plug within a reamed bone, such as a reamed medullary canal of a femur, to halt the progression of bone cement within the bone when an orthopedic implant is being mounted on the bone. Surgical implant 10 can have still other uses as will be appreciated by those skilled in the art.

As shown in FIG. 1, surgical implant 10 comprises a top end plate 12, a bottom end plate 14 spaced apart from top end plate 12, and a plurality of beams 16A-D extending between top end plate 12 and bottom end pate 14. In general, top end plate 12 comprises an outside face 18, an inside face 20, and a side wall extending therebetween. Although not required, in the embodiment depicted outside face 18 and inside face 20 are substantially planar. Outside face 20 is fully, openly exposed while at least a portion of inside face 20 is openly exposed.

Figure 2:
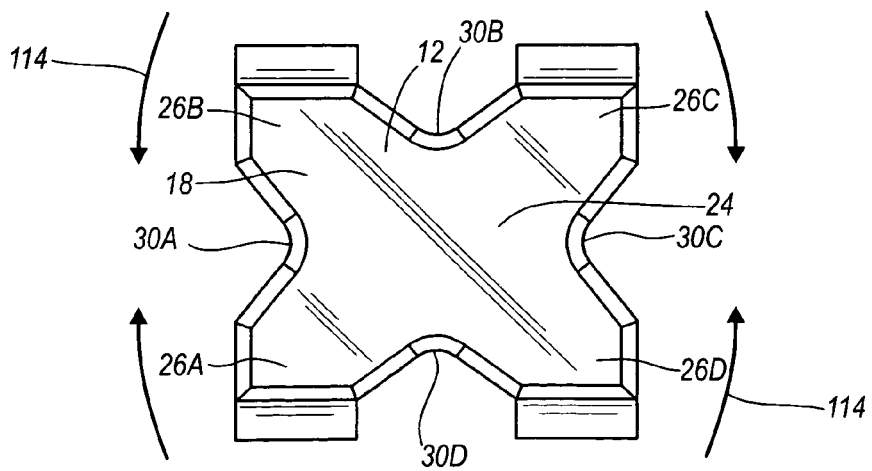
FIG. 2 is a top plan view of the surgical implant shown in FIG. 1.

As depicted in FIGS. 1 and 2, top end plate 12 can be defined as comprising a central portion 24 having four legs 26A-D projecting from central portion 24 in a cantilever fashion and within a common plane so that top end plate 12 has a substantially X-shaped configuration. Each leg 26A-D terminates at a corresponding point corner 28A-D. Likewise, each leg 26A-D is separated by a notch. Specifically, notches 30A-D are formed on side wall 22 of top end plate 12 extending between outside face 18 and inside face 20 at corresponding central locations between each pair of legs 16A-D. It is appreciated that notches 30A-D can have a variety of different configurations. For example, notches 30A-D can have a substantially U- or V-Shaped configuration or be other shapes. If desired, the intersection between outside face 18 and side wall 22 can be beveled.

Figure 3:
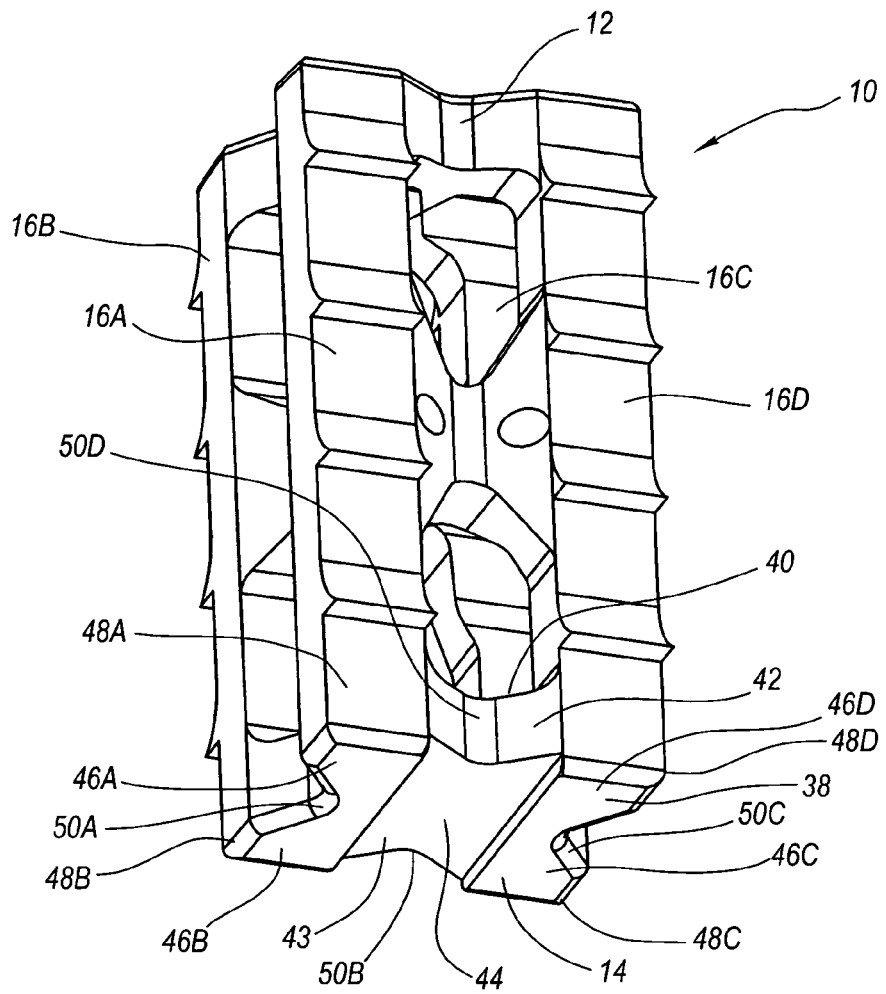
FIG. 3 is a bottom perspective view of the surgical implant shown in FIG. 1.
Figure 4:
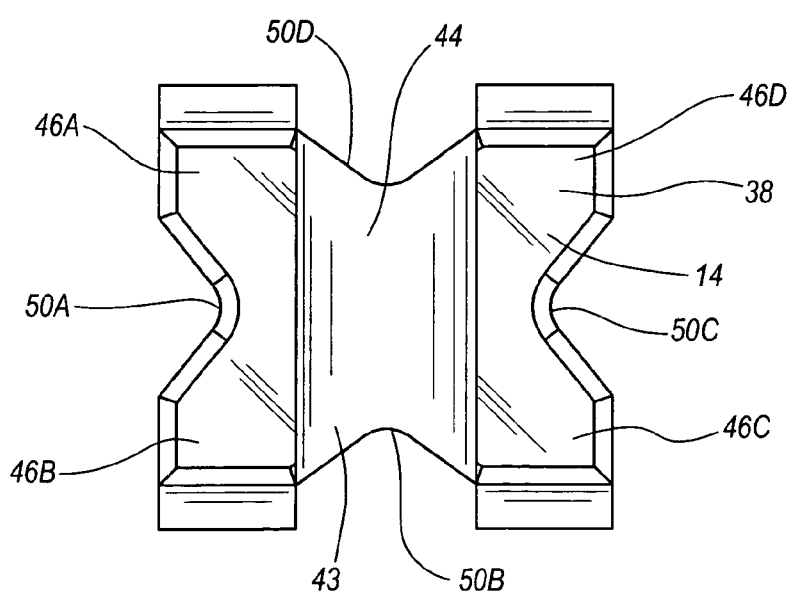
FIG. 4 is a bottom plan view of the surgical implant shown in FIG. 1.

Bottom end plate 14 can have the same configuration as top end plate 12. For example, as depicted in FIGS. 3 and 4, bottom end plate has an outside face 38, an inside face 40, and a side wall 42 extending therebetween. Outside face 38 can be disposed parallel to outside face 18. In one elective contrast between end plates 12 and 14, bottom end plate 14 can have a recessed track 43 extending across outside face 38. Recessed track 43 can be used for proper alignment and engagement with an insertion tool. Again, outside face 38 is fully, openly exposed while at least a portion of inside face 40 is openly exposed.

Bottom end plate 14 can also be defined as comprising a central portion 44 having four legs 46A-D projecting from central portion 44 in a cantilever fashion and within a common plane so that bottom end plate 14 has a substantially X-shaped configuration. Each leg 46A-D terminates at a corresponding point corner 48A-D. Likewise, each leg 46A-D is separated by a corresponding notch 50A-D are formed on side wall 42 of bottom end plate 14 and extend between outside face 38 and inside face 40 at corresponding central locations between each pair of legs 46A-D. It is appreciated that notches 50A-D can have the same configurations as notches 30A-D.

As depicted in FIGS. 1 and 3, four spaced apart beams 16A-D longitudinally extend from inner face 18 of top end plate 12 to inner face 40 of bottom end plate 14. Specifically each beam 16A-D extends from a leg 26A-D on top end plate 12 to a corresponding leg 46A-D on bottom end plate 14. In the embodiment depicted, beams 16A-D are positioned in alignment with corresponding corners 28A-D and 48A-D. Beams 16A-D can be disposed substantially parallel to one another and substantially perpendicular to both top and bottom end plates 12 and 14. In other embodiments, the beams 16A-D can be convergent, divergent, or combinations thereof.

In the embodiment depicted each beam 16A-D has substantially the same configuration. For example, each beam 16A-D has a substantially square or rectangular transverse cross section and comprises a front face 52 and an opposing back face 54 each extending between an interior face 56 and an opposing exterior face 58. Front face 52 and exterior face 58 each face away from surgical implant 10, while back face 54 and interior face 56 each face toward the interior of surgical implant 10. Beams 16A-D are configured such that each back face 54 faces a corresponding back face of one of the other beams. For example, in the depicted embodiment, back faces 54 of beams 16A and 16B face each other while the corresponding front faces 52 face away from each other. It is appreciated that in alternative embodiments beams 16A-D can have a variety of different transverse cross sectional shapes such as circular, oval, triangular or other polygonal or irregular shapes.

Figure 5:
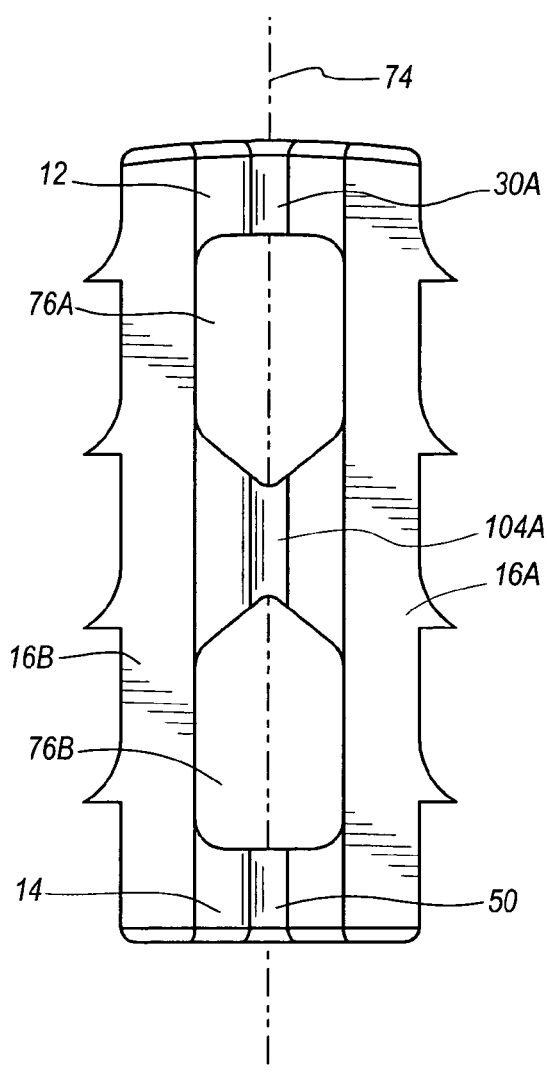
FIG. 5 is an elevated side view of the surgical implant shown in FIG. 1.
Figure 6:
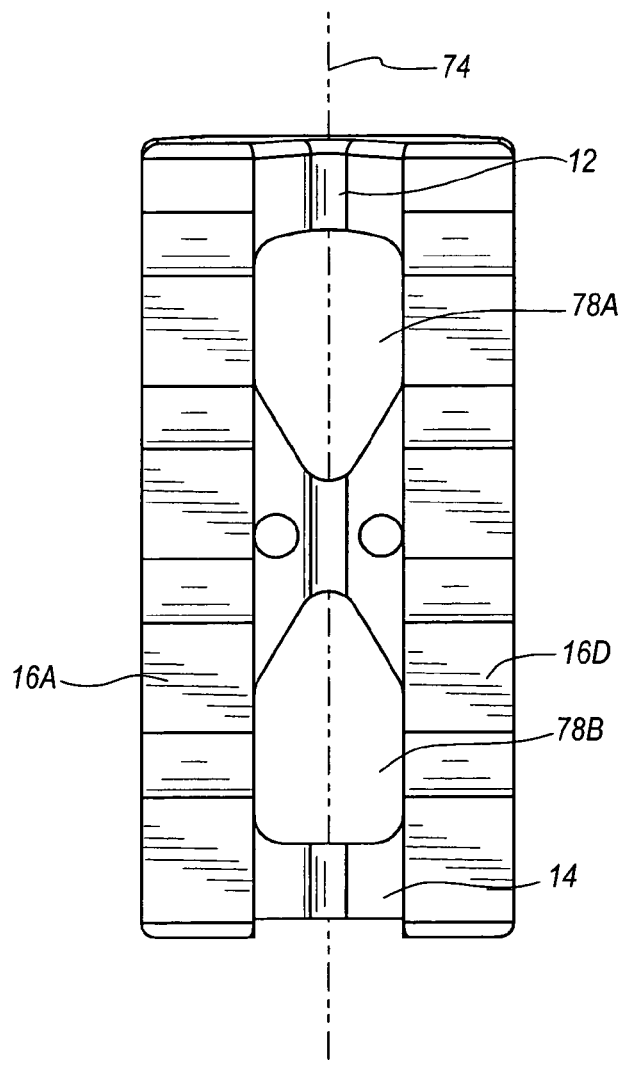
FIG. 6 is an elevated front view of the surgical implant shown in FIG. 1.

In the depicted embodiment beams 16A-D are spaced apart from each other so that openings are formed between beams 16A-D. For example, as shown in FIGS. 1, 5, and 6, a central longitudinal axis 74 is shown centrally extending through top end plate 12 and bottom end plate 14. Beams 16A-D are spaced apart from central longitudinal axis 74 so that inside face 20 of top end plate 12 and inside face 40 of bottom end plate 14 at the location of central longitudinal axis 74 are openly exposed. Furthermore, passageways 76A and B pass between beams 16A and B and between beams 16C and D so as to intersect and pass through central longitudinal axis 74. Passageways 78A and B pass between beams 16A and D and beams 16B and C so as to also intersect and pass through central longitudinal axis 74. Passageways 76A and 78A and passageways 76B and 78B also intersect with each other.

Although not required, each beam 16A-D can also contain one or more retention barbs 64. Each retention barb 64 is formed on or arises out of front face 52 of each beam 16A-D. In the depicted embodiment, barb 64 comprises a flat face 66 arising substantially perpendicular out of front face 52 and facing bottom end plate 14. Each retention barb 34 also has a sloping face 68 arising out of front face 52 and facing top end plate 12. Sloping face 68 can be curved or linear. Faces 66 and 68 intersect to form a top ridge 70. Barbs 64 function to secure surgical implant 10 in place. For example, as surgical implant 10 is slid between adjacent vertebrae beginning with top end plate 12, the sloping orientation of sloping faces 68 enables surgical implant 10 to slide between the vertebrae with barbs 64 riding against the vertebrae. Once in place, however, top ridge 70 and the formation of flat face 66 prevents surgical implant 10 from unintentionally sliding back from between the vertebrae.

It is appreciated that barbs 64 can come in a variety of different sizes, shapes and configurations. For example, in the depicted embodiment barbs 64 span the width of beams 16A-

D. In other embodiments, barbs 34 need not be as wide as beams 16A-D. In some embodiments, sides 56 and 58 of one or more of beams 16A-D angle in towards each other, causing ridge 56 to be shorter or to arise to a point instead of a ridge. Barbs 64 are typically spaced apart on front face 52. In the depicted embodiment there are four barbs 64 on each beam 16A-D. In other embodiments, the number of barbs 64 on each beam 16A-D can vary. For example, a beam can have one, two, or five or more barbs 64. Barbs 64 can be located on a subset of all beams 16A-D or on one end of any beam 16A-D. In one embodiment, side 66 of barb 64 can have the same configuration as side 68. Furthermore, barbs 64 can have a variety of other geometric shapes, such as conical or pyramidal, that will allow barbs 64 to perform their intended function.

Although not required, in one embodiment a support structure 90 is centrally formed between top end plate 12 and bottom end plate 14 at a location spaced apart from top end plate 12 and bottom end plate 14. Depending on the intended use, support structure 90 can be located closer to top end plate 12 or bottom end plate 14. Support structure 90 connects with each of beams 16A-D so as to structurally reinforce beams 16A-D.

Figure 7:
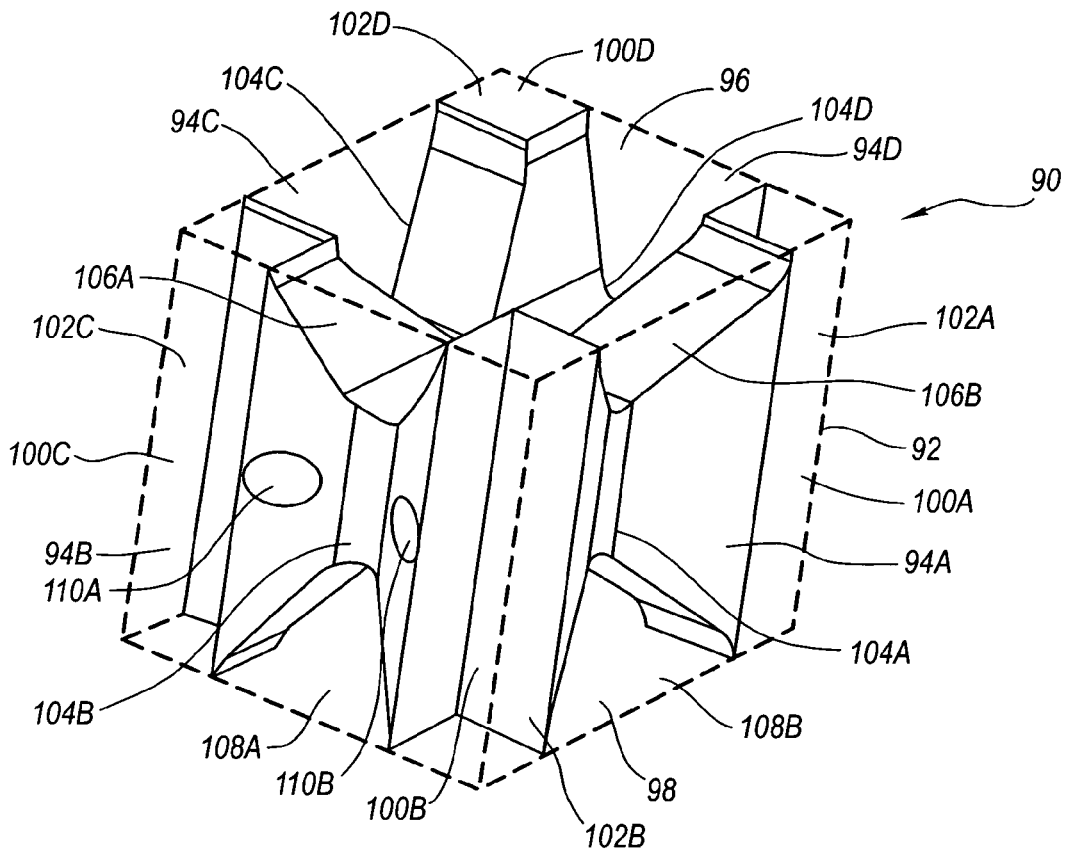
FIG. 7 is a perspective view of the support structure of the surgical implant shown in FIG. 1.

Support structure 90 can have a variety of different configurations and can be defined or expressed in a variety of different ways. In one embodiment support structure 90 can be defined as comprising a six-faced body, such as a polyhedron, having a plurality of channels formed thereon. In the embodiment depicted in FIG. 7, support structure 90 comprises a six-faced polyhedron body 92 defined by dashed lines. Body 92 is shown as being a parallelepiped structure, although other configurations can also be used. Body 92 comprises four side faces 94A-D that each extend between a top face 96 and an opposing bottom face 98. Each pair of adjacent side faces 94A-D intersect along a corresponding side corner 100A-D. Expressed in one form, it can be asserted that corners 100A-D are superimposed on corresponding beams 16A-D, respectively. Expressed in other terms, corners 100A-D are removed so as to form corner channels 102A-D having a configuration complementary to beams 16A-D so that beams 16A-D are received within corresponding corner channels 102A-D.

Formed on each side face 94A-D and extending from bottom face 98 to top face 96 is a corresponding side channel 104A-D, respectively. Although not required, in one embodiment, each side channel 104A-D is aligned with and has a transverse cross section substantially the same as corresponding notches 30A-D formed on top end plate 12 and notches 50A-D formed on bottom end plate 14. For example, as depicted in FIGS. 1 and 5, channel 104A is aligned with notch 30A on top end plate 12 and notch 50A on bottom end plate 14. Both notches 30A, 50A and channel 104A have a substantially V-shaped transverse cross section. Again, however, in other embodiments the configuration of notches 30, 50 and channels 104 can be substantially U-shaped or have other configurations. Each channel 104A-D is shown extending between adjacent side corners 100A-D. In alternative embodiments, channel 104A-D can be narrower and thus need not extend all the way between adjacent side corners 100A-D.

Returning to FIG. 7, in one embodiment support structure 90 can be formed so that top face 96 and bottom face 98 remain substantially flat. In the depicted embodiment, however, a top channel 106A is formed on top surface 96 extending from side face 94B to side face 94D. Likewise, a top channel 106B is formed on top surface 96 and extends from side face 94A to side face 94B. Top channels 106A and B centrally intersect on support structure 90. Each top channel 106A and B can have substantially the same transverse cross section as side channels 104A-D. For example, side channels 106A and B can have a substantially V- or U-shaped transverse cross section or the cross section can be other configurations.

Bottom face 98 has substantially the same configuration as top face 96. As such, a bottom channel 108A is formed on bottom surface 98 extending from side face 94B to side face 94D. Likewise, a bottom channel 108B is formed on bottom surface 98 and extends from side face 94A to side face 94B. Bottom channels 108A and B centrally intersect on support structure 90 and can have substantially the same transverse cross section as top channels 106A and B. Support structure 90 also has a pair of spaced apart, bounded tunnels 110A and B that transversely extend from side face 94B to 94D.

Support structure 90 can be formed so that central longitudinal axis 74 centrally extends through support structure. As a result, passages 76A and B and passages 78A and B, as previously discussed with regard to FIGS. 1, 5 and 6, extend through surgical implant 10 on opposing sides of support structure 90. That is, passages 76A and B are at least partially bounded between inside face 20 of top end plate 12 and the top face 96 of support structure 90. Likewise passages 78A and B are at least partially bounded between inside face 40 of bottom end plate 14 and the bottom face 98 of support structure 90. In other embodiments, the size, shape, and number of passages 76 and 78 can vary depending on any of a number of factors, including the configuration of the beams, the size of the surgical implant, the size and shape of the support structure, and other factors.

Surgical implant 10 is typically formed as a single, integral structure. That is, end plates 12, 14, beams 16A-D, and support structure 90 are integrally formed together. In other embodiments all or some of the components can be separately made and connected together. Surgical implant 10 and/or the components thereof can be produced using any conventional manufacturing technique such as molding, cutting, milling, or the like. It is appreciated that surgical implant 10 can have a variety of different sizes depending on the intended use. In one embodiment surgical implant 10 can have a length extending between outside faces of end plates 12 and 14 in a range between about 20 mm to about 26 mm, a height extending between front faces of beams 16A and 16B in a range between about 8 mm to about 20 mm, and a width extending between exterior faces of beams 16A and 16D in a range between 8 mm to about 12 mm. Other dimensions can also be used.

Surgical implant 10 and/or the components thereof are typically made from a medical grade biocompatible material. In one embodiment, surgical implant 10 is formed from a polyetheretherketone polymer that can be reinforced with a fiber, such as carbon fiber, or other additive. In alternative embodiments, surgical implant 10 and/or the components thereof can be formed from medical grade biocompatible metals, alloys, polymers, ceramics, or other materials that have adequate strength and flexibility. Such materials can be bioabsorbable. It is also appreciated that different components can be made from different materials.

During use, the various passages, channels, and notches of surgical implant 10 can be packed with an osteogenic substance that enhances bone growth. The osteogenic substance can be autogenous bone graft, bone allograft, bone morphogenic it protein (BPM) or other conventional osteogenic substances. The osteogenic substance can be packed directly into surgical implant 10 or can be impregnated into a matrix, such as a sponge, that is then packed into surgical implant 10.

Figure 8:
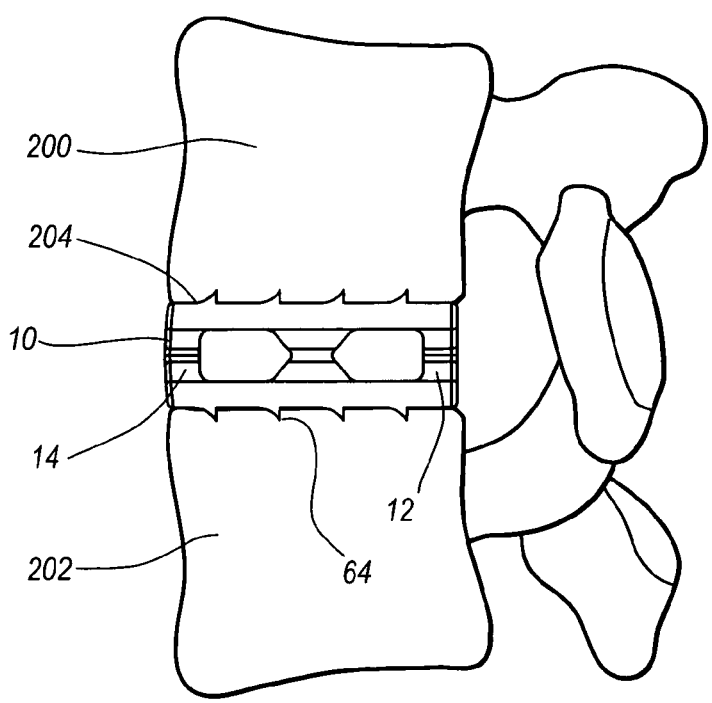
FIG. 8 is a side view of the surgical implant shown in FIG. 1 installed in an intervertebral space.

Although surgical implant 10 can be used for fusing together a variety of different bone structures, illustrated in FIG. 8 is one example where surgical implant 10 is used to fuse together adjacent vertebrae in a spinal column. Specifically, depicted in FIG. 8 is a pair of adjacent vertebrae 200 and 202. A posterior opening has been made through the back of a patient so as to expose vertebrae 200 and 202. A disk or portion of a disk has been removed from between vertebrae 200 and 202 so that a gap 204 is formed therebetween. A surgical implant 10 is selected having a size complementary to gap 204. Once surgical implant 10 is packed with an osteogenic substance, as discussed above, an insertion tool (not shown) is removably coupled with surgical implant 10 and is used to insert surgical implant 10 within gap 204. Surgical implant 10 is inserted with top end plate 12 first so that barbs 64 engage with vertebrae 200 and 202, thereby helping minimize unwanted movement of surgical implant 10 relative to vertebrae 200 and 202.

During postoperative recovery, surgical implant 10 is naturally loaded under compression between vertebrae 200 and 202. As surgical implant 10 is loaded in compression, the force applied to beams 16A-D and end plates 12 and 14, causes cantilevered legs 26A-D of top end plate 12, cantilevered legs 46A-D of bottom end plate 14, and the corner sections of support structure 90 to flex toward each other. For example, as depicted in FIG. 2, legs 26A and 26B flex toward each other in the direction of arrows 114 while legs 26C and 26D also flex toward each other in the direction of arrows 114. In turn, the flexing of the legs 26 and 46 causes beams 16A-D to move toward each other. In so doing, surgical implant 10 is compressed which in turn compresses the osteogenic substance packed within surgical implant 10. As discussed in the background section, proper loading or compressing of the osteogenic substance optimizes the functional operation of the osteogenic substance in developing bone growth that fuses vertebrae 200 and 202 together. It is appreciated that the various notches and channels formed on ends plates 12 and 14 and support structure 90 are, in part, designed to facilitate the desired flexing.

Surgical implant 10 is thus designed to minimize stress shielding by enabling flexing of surgical implant 10 when subject to a compressive load. In turn, flexing of surgical implant 10 facilitates compression of the osteogenic substance packed therein. Surgical implant 10 is also designed so as to maximize the channels, passages, and other openings thereon so as to optimize packing of the osteogenic substance.

Maximizing the openings on surgical implant 10 also enables the bony growth produced by the osteogenic substance to freely grow through and around surgical implant 90 so that vertebrae 200 and 202 can most efficiently be fused together. It is appreciated that surgical implant 10 has sufficient structural strength to prevent over flexing and unwanted failure. Furthermore, the various channels and notches can be altered or varied so as to adjust the flexibility either uniformly or at specific locations on surgical implant 10. For example, if desired top end plate 12 can be formed with notches 30A-D while bottom end plate 14 can be formed without notches 50A-D or with smaller notches. In this design, top end plate 12 would have greater flexibility than bottom end plate 14.

Figure 9:
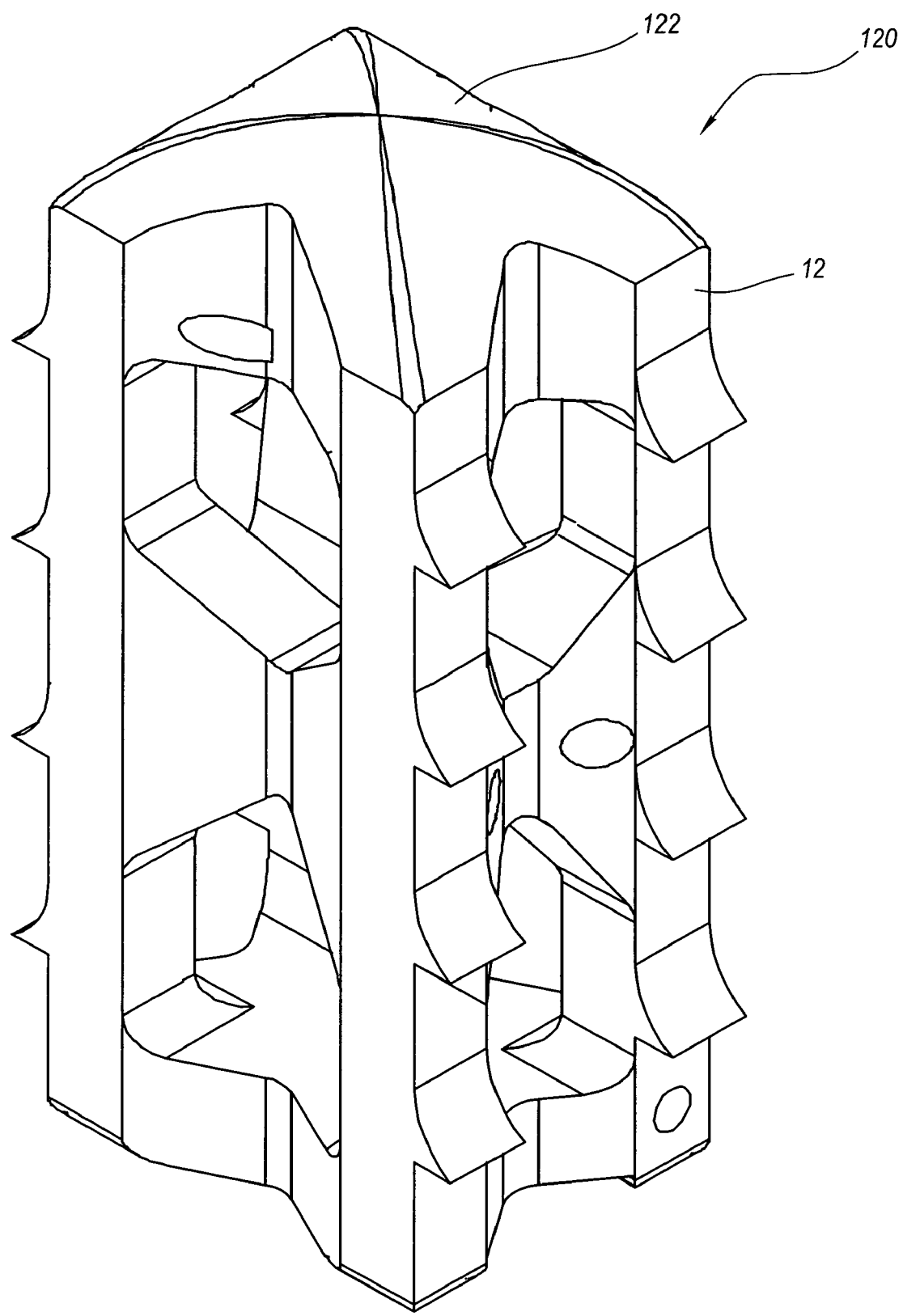
FIG. 9 is a perspective view of an alternative design of the surgical implant shown in FIG. 1 having a rounded nose.
Figure 10:
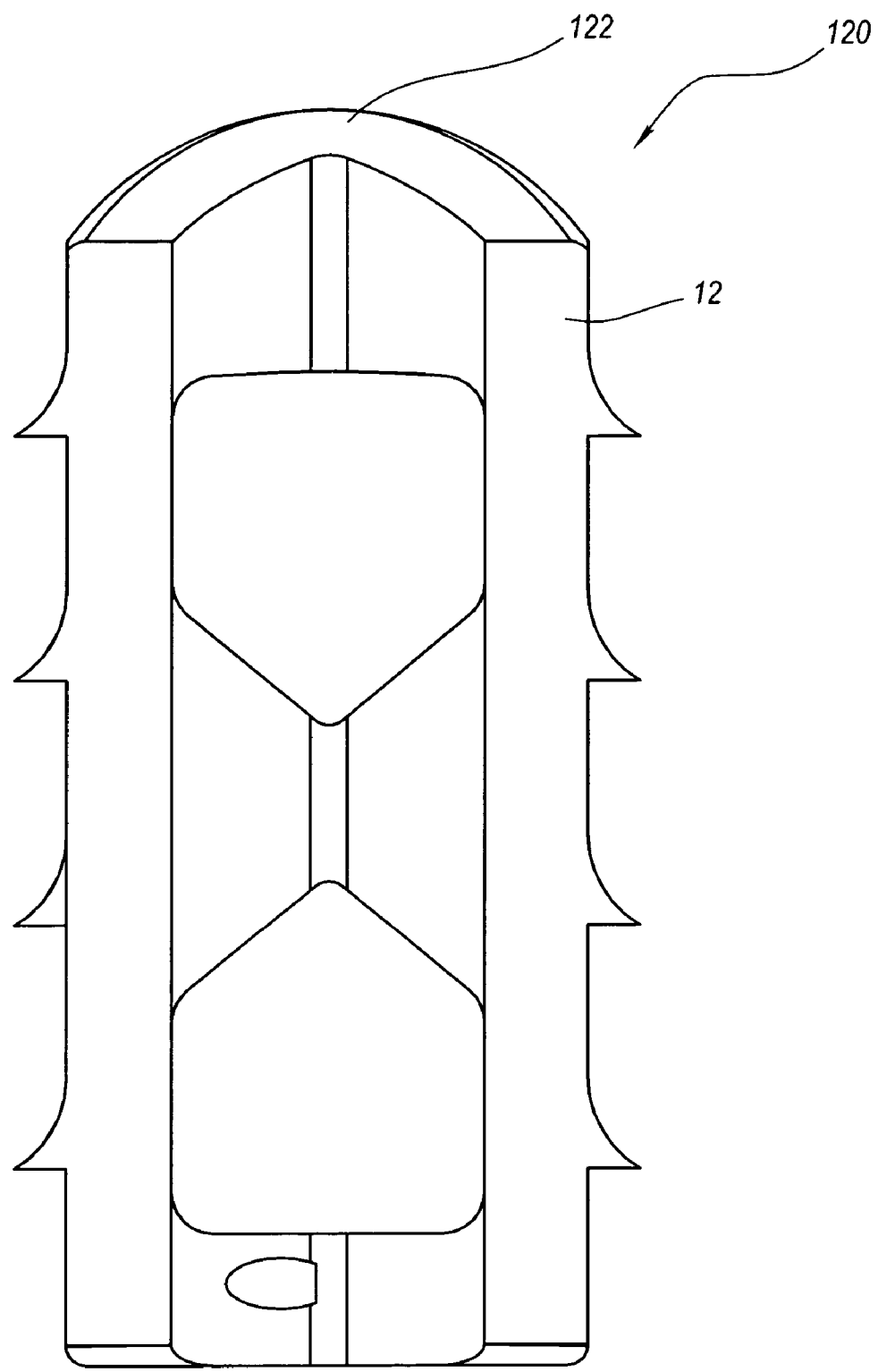
FIG. 10 is an elevated side view of the implant shown in FIG. 9.

Depicted in FIGS. 9 and 10 is an alternative embodiment of a surgical implant 120 wherein like elements between surgical implants 10 and 120 are identified by like reference characters. Surgical implants 10 and 120 are substantially identical except that in contrast to outside face 18 of top end plate 12 being flat in surgical implant 10, surgical implant 120 comprises top end plate 12 having an outside face 18 in the form of a rounded, outwardly projecting nose 122. Rounded nose 122 can provide for easier insertion of the surgical implant.

Figure 11:
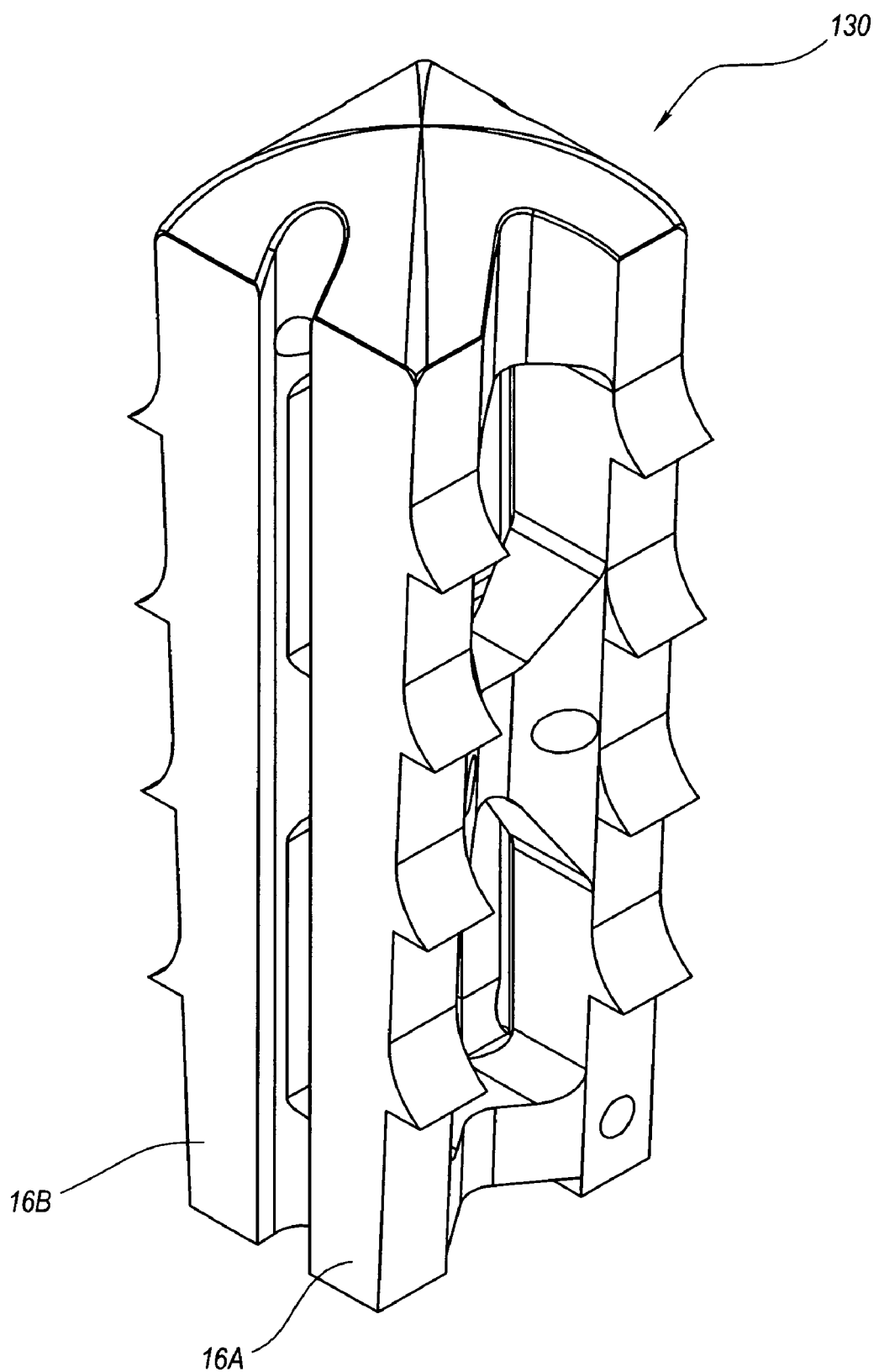
FIG. 11 is a perspective view of an alternative design of the surgical implant shown in FIG. 9 wherein the surgical implant is tapered along the length thereof.
Figure 12:
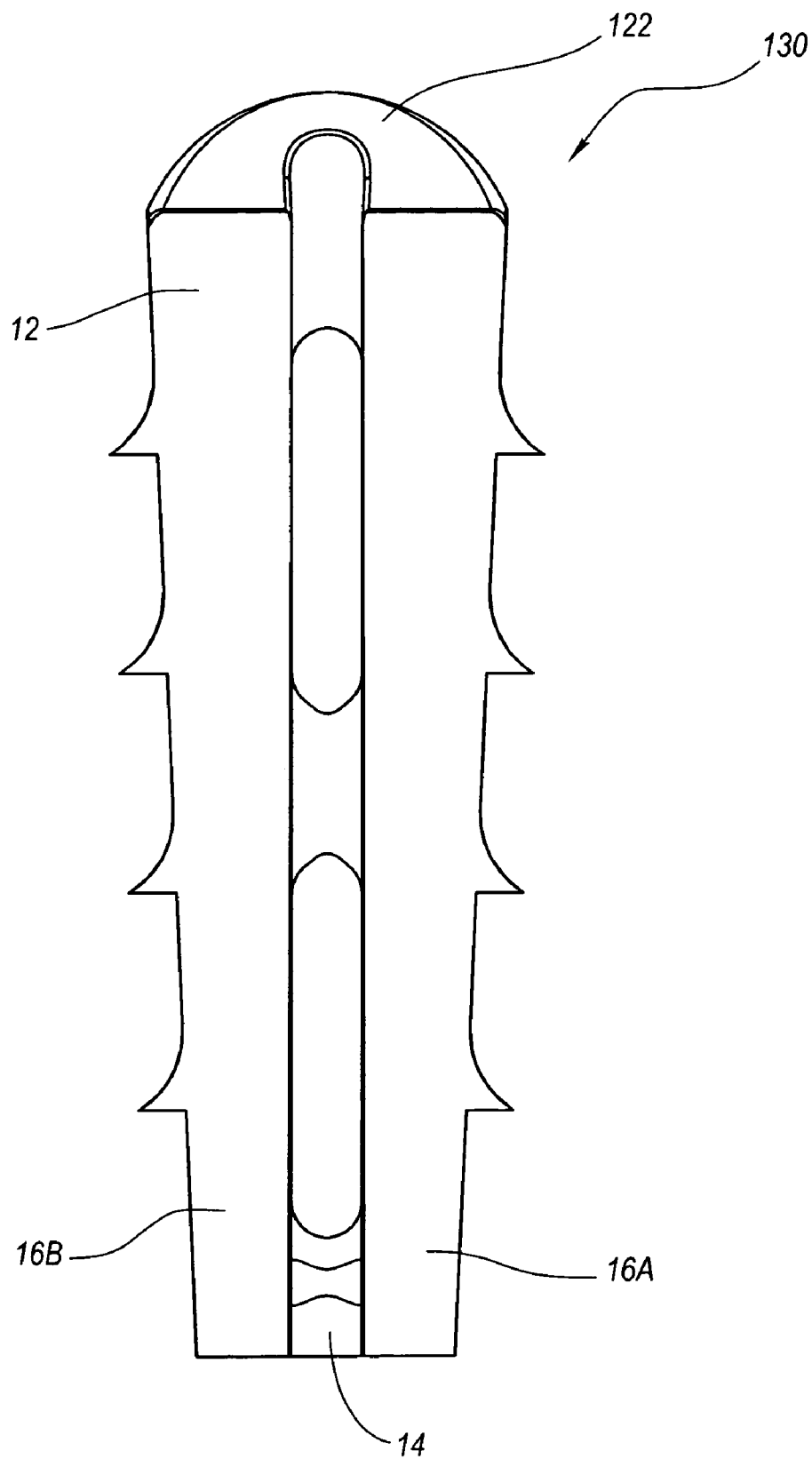
FIG. 12 is an elevated side view of the surgical implant shown in FIG. 11.
Figure 13:
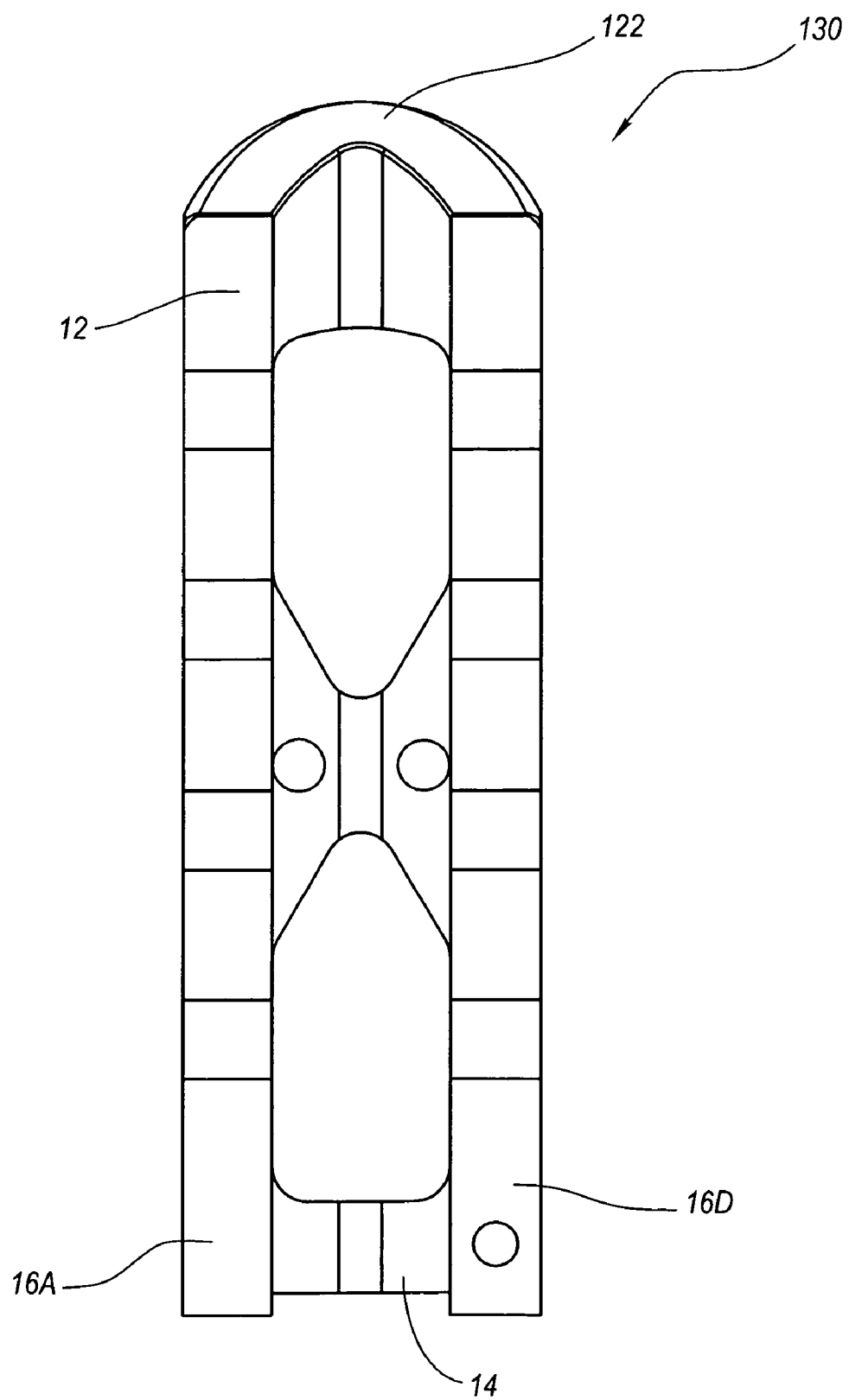
FIG. 13 is an elevated front view of the surgical implant shown in FIG. 11.

Depicted in FIGS. 11-13 is another embodiment of a surgical implant 130 wherein like elements are identified by like reference characters. In contrast to surgical implant 10 wherein all of beams 16A-D are evenly spaced along the length of surgical implant 10, surgical implant 130 is tapered along the length thereof. Specifically, as depicted in FIGS. 11 and 12, the distance between beams 16A and 16B tapers from far apart at top end plate 12 to closer together at bottom end plate 14. Beams 16C and 16D are also correspondingly tapered. However, as depicted in FIG. 13, the spacing between beams 16A and 16D remains substantially constant along the length of surgical implant 130. Beams 16B and 16C are also correspondingly spaced. To account for the tapering, bottom end plate 14 is smaller than top end plate 12. The tapering of the beams results in surgical implant 130 having a substantially wedged shaped configuration. Because the gap between vertebrae 200 and 202 is typically wedged shaped, surgical implant 130 can be sized to more anatomically fit within the space between adjacent vertebrae.

The inventive surgical implants as disclosed herein have a number of unique, discrete features that can be used independently or in combinations. The various features produce a number of unique advantages. For example, the unitary design of the surgical implants makes them simple to use and operate. Select designs of the various surgical implants also provide for desired flexing along the length thereof. The flexing can be uniform or varied along the length of the surgical implants. Such flexing minimizes stress shielding while optimizing the production of bone growth by properly compressing the osteogenic substance packed within the surgical implants. The open passages, channels, and notches through and along the surgical implants also optimize packing of osteogenic substance and promote unrestricted growth of bone through and around the implants so as to optimize bone fusion. The surgical implants have numerous other benefits that will be apparent to those skilled in the art.

The present invention may be embodied in other specific forms without departing from its spirit or essential characteristics. The described embodiments are to be considered in all respects only as illustrative and not restrictive. The scope of the invention is, therefore, indicated by the appended claims rather that by the foregoing description. All changes which come within the meaning and range of equivalency of the claims are to be embraced within their scope.

What is claimed is:

1. A surgical implant comprising:
    a first end plate having four sides and four corners, a substantially V-shaped notch being formed on each side between each adjacent pair of corners so as to give the first end plate a substantially X-shaped configuration;
    a second end plate spaced apart from the first end plate, a central longitudinal axis centrally extending between the first end plate and the second end plate;
    four spaced apart beams extending from the first end plate to the second end plate at locations spaced apart from the central longitudinal axis, an open passageway extending between each adjacent pair of the beams and intersecting with the central longitudinal axis, wherein the first end plate, the second end plate, and the beams are integrally formed as a one piece construction from a single piece of material and wherein each of the beams has a planar bearing surface, the planar bearing surfaces of two adjacent beams being coplanar; and a plurality of retention barbs projecting from each of the planar bearing surfaces that are coplanar, at least a portion of each retention barb outwardly projecting orthogonal to the plane of the planar bearing surfaces.

2. The surgical implant of claim 1, wherein the second end plate has a substantially X-shaped configuration.

3. The surgical implant of claim 1, wherein at least one of the beams has a square or rectangular transverse cross section.

4. The surgical implant of claim 1, further comprising a plurality of retention barbs outwardly projecting from each of the planar bearing surfaces at least a portion of each retention barb outwardly projecting orthogonal to the plane of the planar bearing surface from which it projects.

5. The surgical implant of claim 1, wherein the first end plate has an inside face and an outside face and no bounded holes are formed extending between the inside face and the outside face.

6. The surgical implant of claim 1, wherein the first end plate has an inside face and an outside face, the outside face having the configuration of a rounded, outwardly projecting nose that terminates at a rounded apex.

7. The surgical implant of claim 1, wherein the distance between two adjacent beams tapers along the length between the first end plate and the second end plate.

8. The surgical implant of claim 1, further comprising a support structure disposed between the first end plate and the second end plate at a location spaced apart from the first end plate and the second end plate, the support structure connecting to each of the beams and intersecting with the longitudinal axis.

9. The surgical implant of claim 1, wherein the second end plate has an outside face facing away from the first end plate, the outside face having a recessed track formed therein that extends thereacross.

10. The surgical implant of claim 1, further comprising:
the planar bearing surface of each beam longitudinally extending between the first end plate and the second end plate; and
a plurality of spaced apart retention barbs outwardly projecting from each planar bearing surface in a direction that is substantially orthogonal to the plane of the planar bearing surface.

11. The surgical implant of claim 10, wherein a first two of the planar bearing surfaces both define a common first plane and a second two of the planar bearing surfaces both define a common second plane.

12. The surgical implant of claim 11, wherein the first plane and the second plane are parallel to each other.

13. The surgical implant of claim 1, wherein the surgical implant is comprised of a polyetheretherketone polymer.

14. The surgical implant of claim 1, wherein the substantially V-shaped notch formed between the beams having the planar bearing surfaces disposed within the same plane is formed such that no portion of the surgical implant outwardly extends beyond the plane formed by the planar bearing surfaces.

15. A surgical implant for fusing together two adjacent bones or pieces of bone, the surgical implant comprising:
a first end plate comprising a solid central portion and four legs, each leg outwardly projecting from the central portion to a corner disposed on an outer end of the leg so that the first end plate has a substantially X-shaped configuration, the corners being disposed such that when the first end plate is viewed in a top plan view, an imaginary straight line can be drawn between the corners of opposing legs that continuously remains on or in the first end plate;
a second end plate spaced apart from the first end plate;
a plurality of spaced apart beams, each beam longitudinally extending from a corresponding one of the legs of the first end plate to the second end plate, each of the beams having a planar bearing surface, the planar bearing surfaces of two adjacent beams being coplanar; and
a plurality of retention barbs projecting from each of the planar bearing surfaces that are coplanar, at least a portion of each retention barb outwardly projecting orthogonal to the plane of the planar bearing surfaces.

16. The surgical implant of claim 15, wherein the second end plate comprises a central portion and four legs outwardly projecting from the central portion so that the second end plate has a substantially X-shaped configuration.

17. The surgical implant of claim 16, wherein the second end plate is substantially the same size and shape as the first end plate.

18. The surgical implant of claim 16, wherein each of the spaced apart beams extends to a corresponding one of the legs of the second end plate.

19. The surgical implant of claim 16, wherein the first end plate has an inside face facing the second end plate, the inside face having a central portion that is openly exposed.

20. The surgical implant of claim 16, wherein a central longitudinal axis centrally extends between the first end plate and the second end plate, an open passageway extends between each adjacent pair of the beams and intersects with the central longitudinal axis.

21. The surgical implant of claim 20, further comprising a support structure disposed between the first end plate and the second end plate at a location spaced apart from the first end plate and the second end plate, the support structure connecting to each of the beams and intersecting with the central longitudinal axis.

22. The surgical implant of claim 16, wherein the first end plate has an inside face and an outside face, the outside face having the configuration of a rounded, outwardly projecting nose that terminates at a rounded apex.

23. The surgical implant of claim 16, wherein the distance between two adjacent beams tapers along the length between the first end plate and the second end plate.

24. The surgical implant of claim 16, further comprising a plurality of spaced apart retention barbs disposed along the planar bearing surface of each beam so as to outwardly project from the planar bearing surface in a direction that is substantially orthogonal to the plane of the planar bearing surface.

25. The surgical implant of claim 16, wherein the legs to which adjacent beams are connected move toward one another, but do not touch one another in response to the application of a compressive force between the adjacent beams.

26. The surgical implant of claim 16, wherein each of the plurality of beams has a square or rectangular transverse cross-sectional shape.

27. The surgical implant of claim 15, further comprising:
the planar bearing surface of each beam longitudinally extending between the first end plate and the second end plate;
a plurality of spaced apart retention barbs outwardly projecting from each planar bearing surface in a direction that is substantially orthogonal to the plane of the planar bearing surface; and a first two of the planar bearing surfaces both define a common first plane and a second two of the planar bearing surfaces both define a common second plane.

28. A surgical implant for fusing two adjacent bones or pieces of bone, the implant comprising:
a first end plate;
a second end plate spaced apart from the first end plate along a central longitudinal axis;
four spaced apart beams longitudinally extending from the first end plate to the second end plate; and
a support structure positioned between the first and second end plates at a location spaced apart from the first and second end plates, the support structure comprising a body having four side faces each extending between a top face and an opposing bottom face, the top and bottom faces each intersecting the central longitudinal axis, the side faces each facing a separate direction away from and not intersecting the central longitudinal axis, each pair of adjacent side faces intersecting along a side corner that is superimposed within a corresponding beam, a separate channel being formed on each side face, each channel extending in the longitudinal direction from the top face to the bottom face so as not to intersect the central longitudinal axis, a first top channel being recessed on the top face of the body and extending between two of the side faces of the body.

29. The surgical implant of claim 28, wherein the support structure further comprises a second top channel recessed on the top face of the body and extending between the other two side faces such that the first top channel and the second top channel intersect.

30. The surgical implant of claim 29, wherein the support structure further comprises:
a first bottom channel recessed on the bottom face of the body and extending between two of the side faces; and
a second bottom channel recessed on the bottom face of the body and extending between the other two side faces such that the first bottom channel and the second bottom channel intersect.

31. The surgical implant of claim 30, wherein a first bottom channel recessed on the bottom face of the body of the support structure has a substantially V- or U-shaped configuration.

32. The surgical implant of claim 28, wherein each channel of the support structure has a substantially U- or V-shaped configuration.

33. The surgical implant of claim 28, further comprising at least one bounded tunnel transversely extending through the support structure between two of the side faces.

34. The surgical implant of claim 28, wherein the support structure has a substantially X-shaped configuration when viewed in a central transverse cross-section.

35. The surgical implant of claim 28, wherein the support structure and the beams and the end plates are integrally formed as a unitary structure from a single piece of material.

36. The surgical implant of claim 28, wherein a central longitudinal axis centrally extends between the first end plate and the second end plate and intersects with the support structure, and an open passageway extends between each adjacent pair of the beams and intersects with the central longitudinal axis.

37. The surgical implant of claim 28, wherein:
the first end plate comprises a solid central portion and four legs outwardly projecting from the central portion so that the first end plate has a substantially X-shaped configuration;
the second end plate comprises a solid central portion and four legs outwardly projecting from the central portion so that the second end plate has a substantially X-shaped configuration; and
each beam extends from a corresponding leg of the first end plate to a corresponding leg of the second end plate.

38. The surgical implant of claim 28, wherein the first top channel recessed on the top face of the body of the support structure has a substantially V- or U-shaped configuration.

39. A surgical implant comprising:
a first end plate having four sides and four corners, a V-shaped notch being formed on each side between each adjacent pair of corners so as to give the first end plate a substantially X-shaped configuration;
a second end plate spaced apart from the first end plate, a central longitudinal axis centrally extending between the first end plate and the second end plate;
four spaced apart beams extending from the four corners of the first end plate to the second end plate, an open passageway extending between each adjacent pair of the beams and intersecting with the central longitudinal axis,
wherein each of the beams has a planar bearing surface, the planar bearing surfaces of two adjacent beams being coplanar, and wherein the legs to which adjacent beams are connected move toward one another, but do not touch one another in response to the application of a compressive force between the adjacent beams on the bearing surfaces; and
a plurality of retention barbs projecting from each of the planar bearing surfaces that are coplanar, at least a portion of each retention barb outwardly projecting orthogonal to the plane of the planar bearing surfaces.

* * * * *

UNITED STATES PATENT AND TRADEMARK OFFICE
CERTIFICATE OF CORRECTION

PATENT NO. : 7,794,500 B2
APPLICATION NO. : 11/147487
DATED : September 14, 2010
INVENTOR(S) : Felix It is certified that error appears in the above-identified patent and that said Letters Patent is hereby corrected as shown below:

Title Page, Item 57, ABSTRACT
Line 3, change "for" to --from--
Line 7, change "location spaced apart form" to --locations spaced apart from--

Column 1
Line 24, change "vertebra" to --vertebrae--

Column 3
Line 29, change "Outside face 20" to --Outside face 18--
Line 65, after "notch 50A-D" insert --. Notches 50A-D--

Column 4
Line 5, change "inner face 18" to --inside face 20--
Line 6, change "inner face 40" to --inside face 40--

Column 5
Line 1, change "barbs 34" to --barbs 64--
Line 4, change "ridge 56" to --ridge 70--

Column 6
Line 64, remove [it]

Column 7
Line 37, change "ends" to --end--

Column 8
Line 19, change "wedged shaped" to --wedge shaped--
Line 20, change "wedged shaped" to --wedge shaped--
Line 45, change "that" to --than--

Signed and Sealed this
Eighth Day of March, 2011

David J. Kappos
*Director of the United States Patent and Trademark Office*